(12) United States Patent
Kang et al.

(10) Patent No.: US 10,457,949 B2
(45) Date of Patent: Oct. 29, 2019

(54) RDNA NTS-BASED GENE MULTIPLE INSERTION CASSETTE SET AND GRAS-GRADE RECOMBINANT YEAST STRAIN

(71) Applicant: CHUNG-ANG UNIVERSITY INDUSTRY-ACADEMY COOPERATION FOUNDATION, Seoul (KR)

(72) Inventors: Hyun Ah Kang, Daejeon (KR); Hye Yun Moon, Seoul (KR); Hong Jin Kim, Seoul (KR)

(73) Assignee: CHUNG-ANG UNIVERSITY INDUSTRY-ACADEMY COOPERATION FOUNDATION, Seoul (KR)

( * ) Notice: Subject to any disclaimer, the term of this patent is extended or adjusted under 35 U.S.C. 154(b) by 173 days.

(21) Appl. No.: 15/505,252

(22) PCT Filed: Dec. 30, 2014

(86) PCT No.: PCT/KR2014/013047
§ 371 (c)(1),
(2) Date: Feb. 21, 2017

(87) PCT Pub. No.: WO2016/027943
PCT Pub. Date: Feb. 25, 2016

(65) Prior Publication Data
US 2017/0268011 A1 Sep. 21, 2017

(30) Foreign Application Priority Data
Aug. 21, 2014 (KR) .................. 10-2014-0108910

(51) Int. Cl.
*C12N 15/81* (2006.01)
*A61K 39/00* (2006.01)
(Continued)

(52) U.S. Cl.
CPC ............ *C12N 15/81* (2013.01); *A61K 9/0053* (2013.01); *A61K 39/00* (2013.01); *A61K 39/12* (2013.01);
(Continued)

(58) Field of Classification Search
None
See application file for complete search history.

(56) References Cited

U.S. PATENT DOCUMENTS 6,638,735 B1 * 10/2003 Rhee ..................... C07K 14/39
435/254.23
2003/0041349 A1 * 2/2003 Christian ............... A01N 63/00
800/280

(Continued)

FOREIGN PATENT DOCUMENTS

| KR | 10-1999-0033548 A | 5/1999 |
| KR | 10-2003-0072201 A | 9/2003 |
| KR | 10-2005-0077399 A | 8/2005 |

OTHER PUBLICATIONS

Le Borgne, S., Genetic Engineering of Industrial Strains of *Saccharomyces cerevisiae*; Recombinant Gene Expression: Reviews and Protocols, 3rd Ed.: Methods in Molecular Biology, vol. 824, Ch. 24, pp. 451-464, Springer Science+Business Media, 2012 (Year: 2012).*

(Continued)

*Primary Examiner* — Addison D Ault
(74) *Attorney, Agent, or Firm* — Revolution IP, PLLC

(57) ABSTRACT

Disclosed is a gene multiple insertion cassette set including rDNA NTS fragments and an auxotrophic selection marker having an incomplete promoter is developed, and a safe oral recombinant strain having no antibiotic resistant marker is constructed by multiple insertion of an optimum number of the developed gene multiple insertion cassette sets into chromosomes of a *Saccharomyces cerevisiae* strain, a vac- (Continued)

cine composition including, as an active ingredient, the above strain, a culture product thereof, a cell lysate, or nodavirus capsid protein (NNVcp) isolated and purified therefrom, and a composition for feed addition including, as an active ingredient, the above strain, a culture product thereof, a cell lysate, or squalene or oxidosqualene isolated and purified therefrom.

16 Claims, 15 Drawing Sheets

Specification includes a Sequence Listing.

(51) Int. Cl.
  *C12N 15/70*    (2006.01)
  *A61K 9/00*     (2006.01)
  *A61K 39/12*     (2006.01)
  *C07K 14/005*    (2006.01)
  *C12R 1/865*    (2006.01)

(52) U.S. Cl.
  CPC ............ *C07K 14/005* (2013.01); *C12N 15/70* (2013.01); *A61K 2039/523* (2013.01); *A61K 2039/54* (2013.01); *C12N 2770/30022* (2013.01); *C12N 2770/30034* (2013.01); *C12N 2770/30071* (2013.01); *C12R 1/865* (2013.01)

(56) References Cited

U.S. PATENT DOCUMENTS

| | | | |
|---|---|---|---|
| 2007/0154575 A1* | 7/2007 | Shimoda | A61K 31/7008 424/756 |
| 2008/0187940 A1 | 8/2008 | Lim et al. | |
| 2010/0218283 A1* | 8/2010 | Ro | C12N 9/0042 800/317.3 |

OTHER PUBLICATIONS

International Search Report for PCT/KR2014/013047 dated May 12, 2015 from Korean Intellectual Property Office.

Lopes, T. S. et al., "Factors Affecting the Mitotic Stability of High-copy-number Integration into the Ribosomal DNA of *Succhuromyces cerevisiue*", Yeast, Apr. 1996, vol. 12, No. 5, pp. 467-477.

Klabunde, J. et al., "Single-step co-integration of multiple expressible heterologous genes into the ribosomal DNA of the methylotrophic yeast Hansenula polymorpha", Applied Microbiology and Biotechnology, May 2002, vol. 58, No. 6, pp. 797-805.

NCIB, GenBank accession No. FN554374.1 (Dec. 21, 2011).

Moon, Hye Yun et al., "Development of novel multiple gene integrative cassette sets based on rDNA-NTS for construction of vaccine-grade recombinant yeast", In: 2014 International Meeting of The Federation of Korean Microbiological Societies, Oct. 30-Oct. 31, 2014.

* cited by examiner

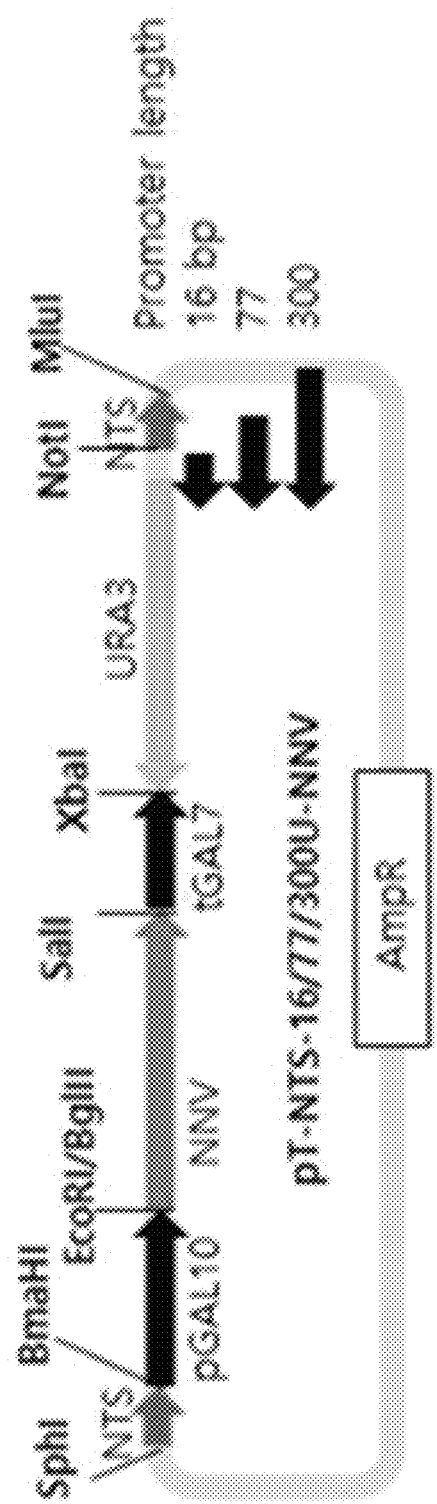
[FIG. 1a]

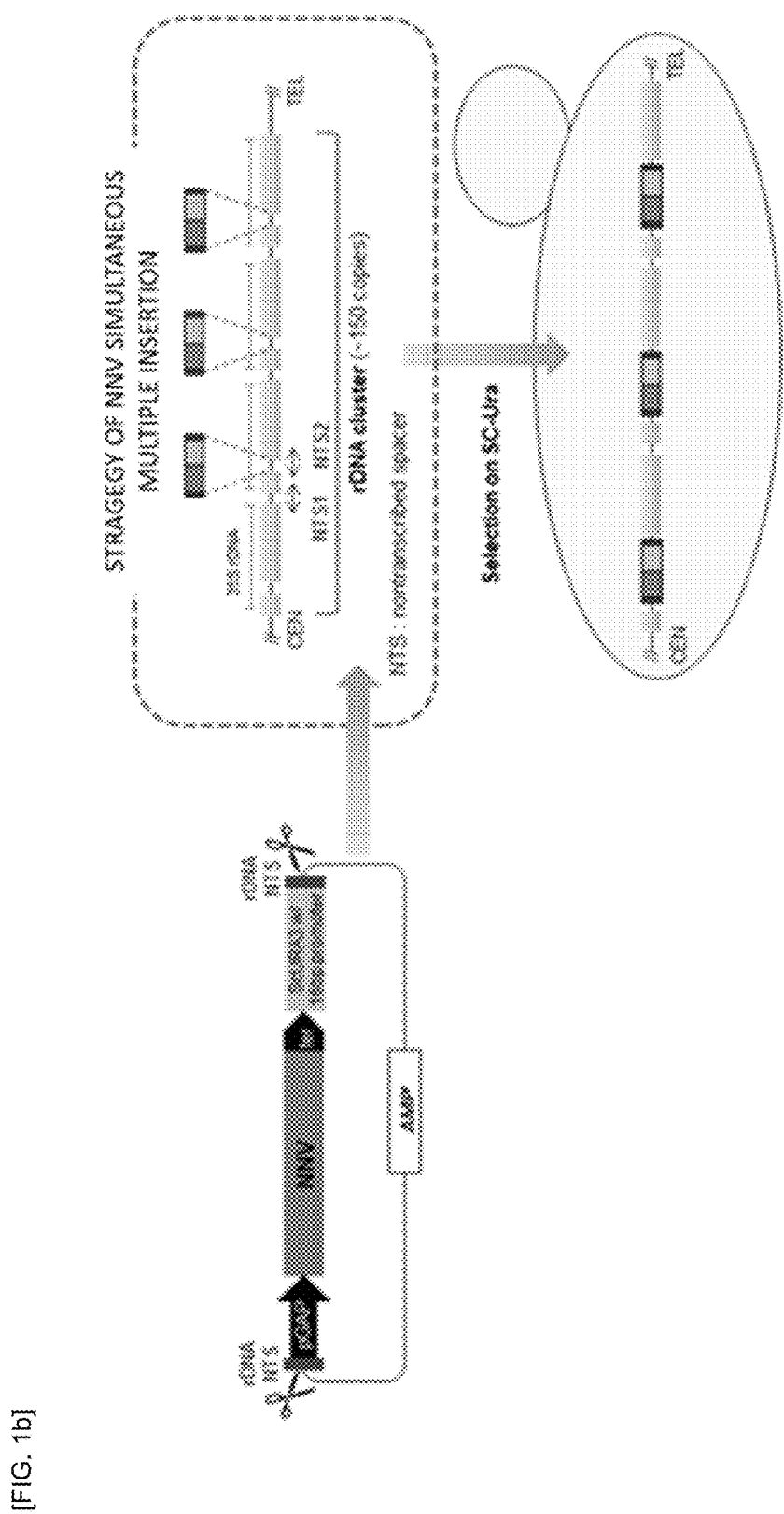
[FIG. 1b]

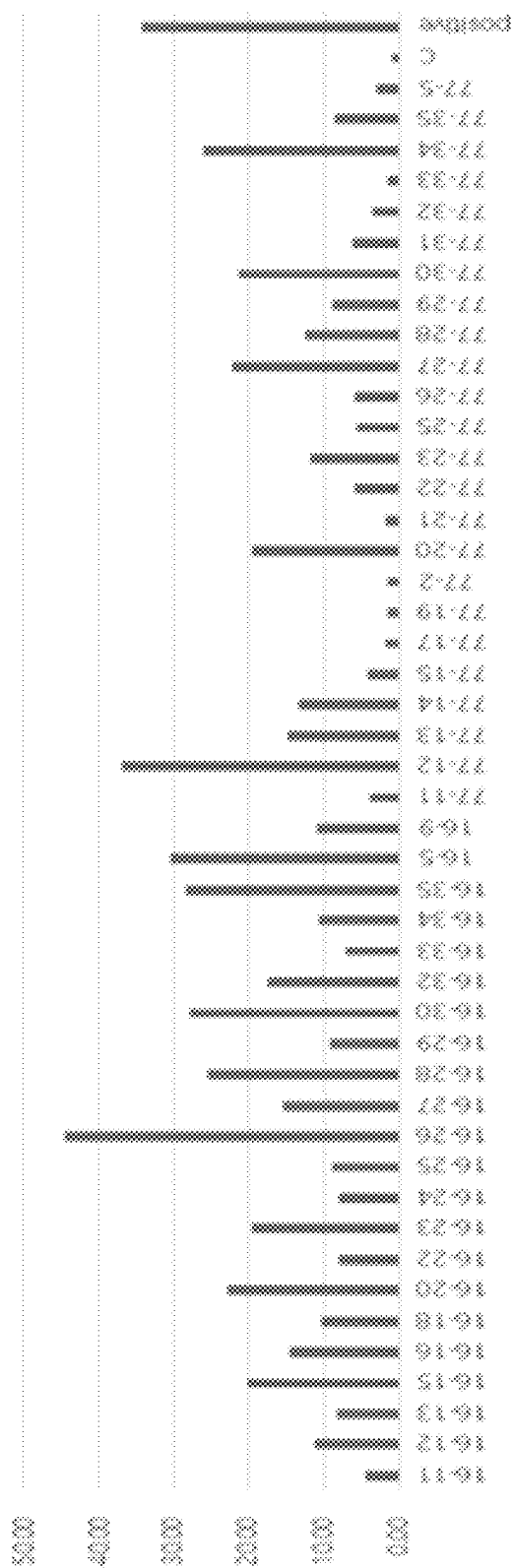
[FIG. 1c]

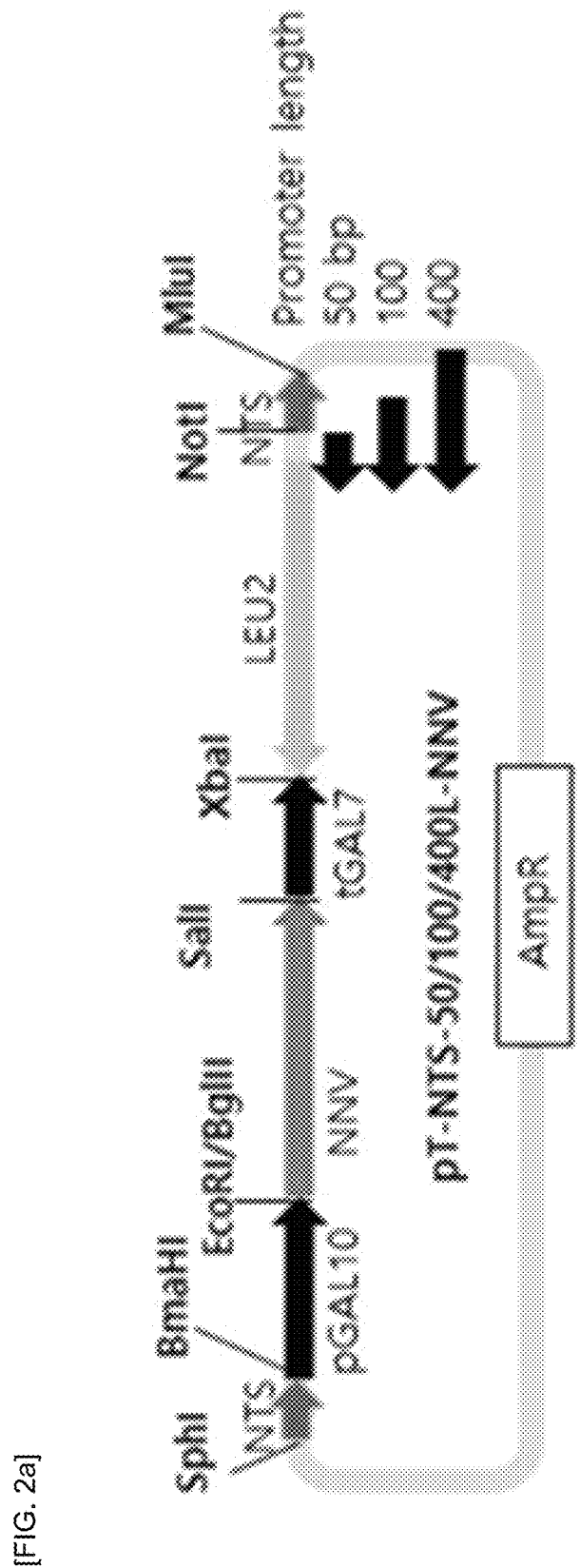
[FIG. 2a]

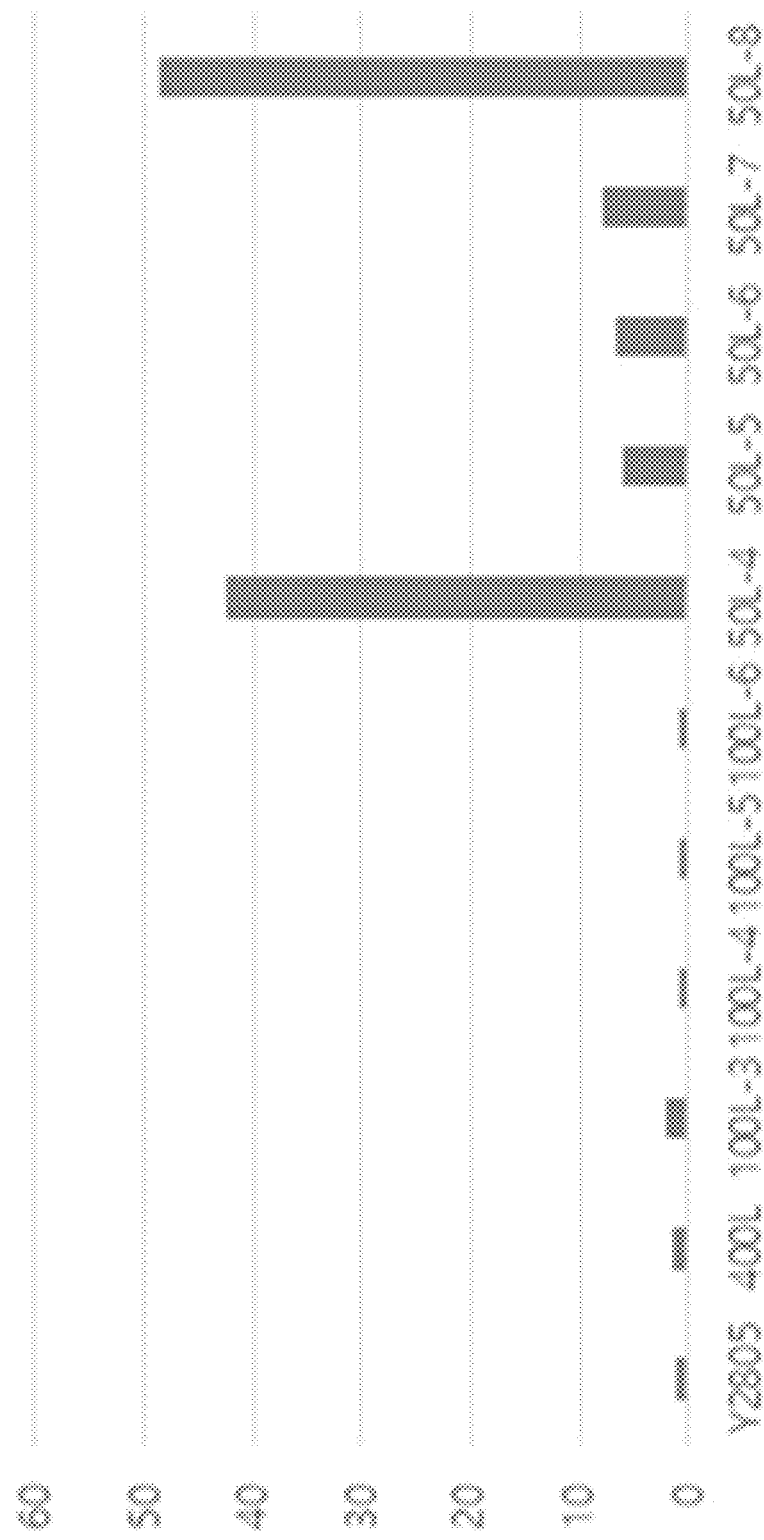
[FIG. 2b]

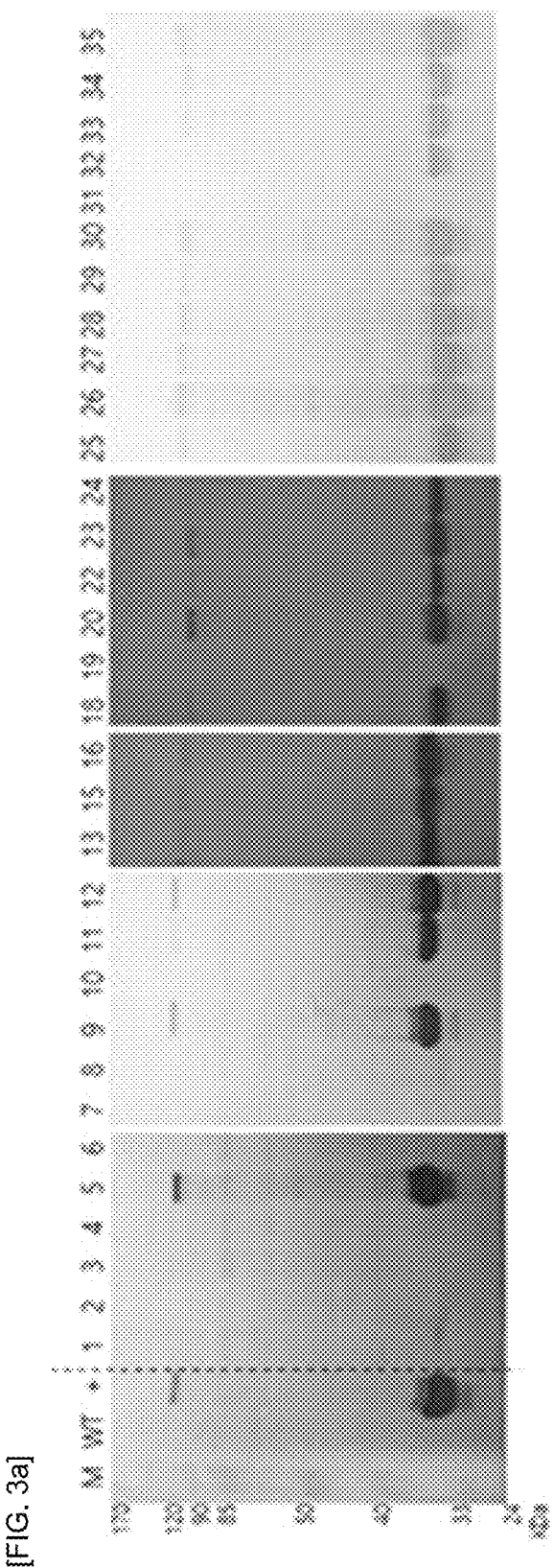
[FIG. 3a]

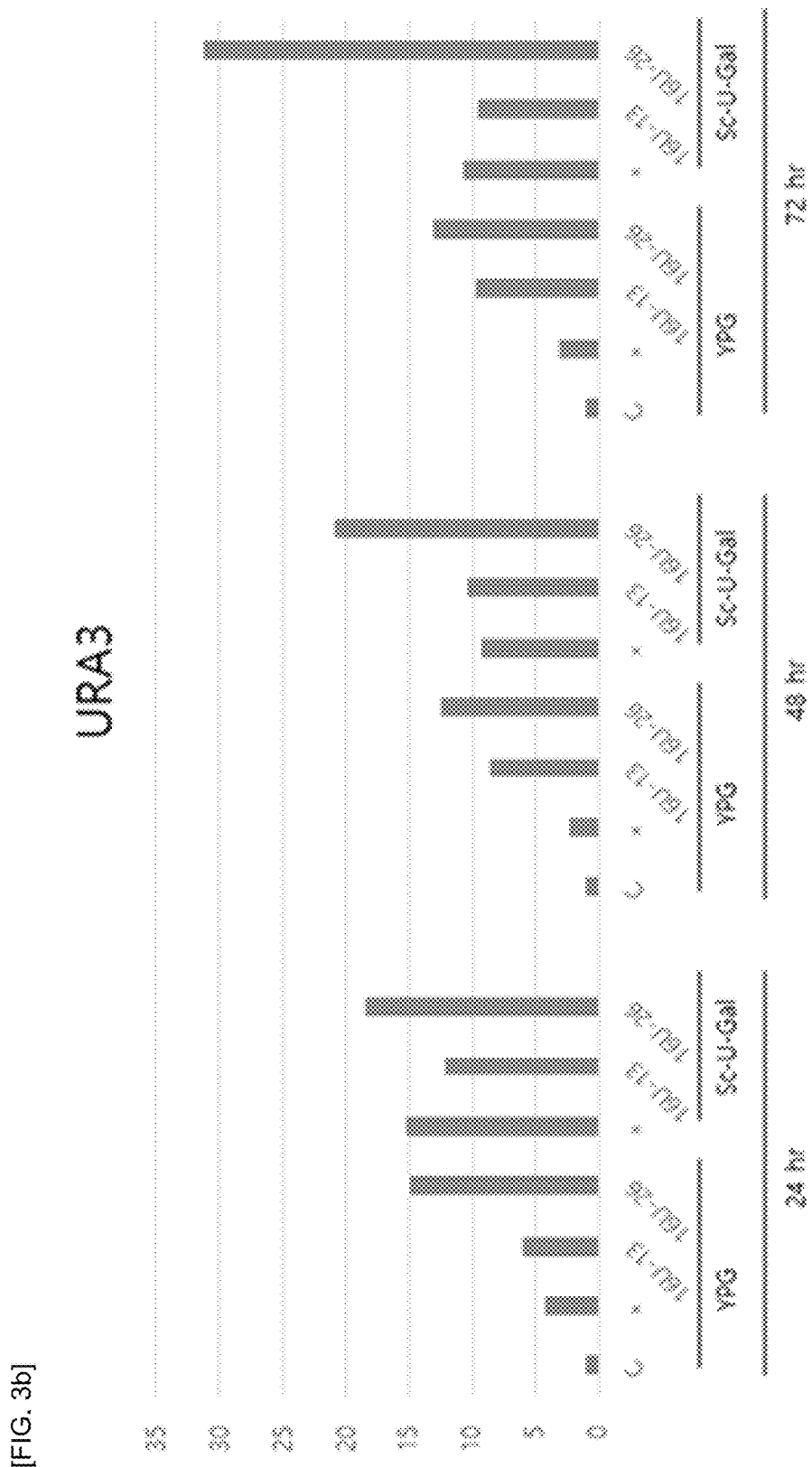
[FIG. 3b]

[FIG. 4]
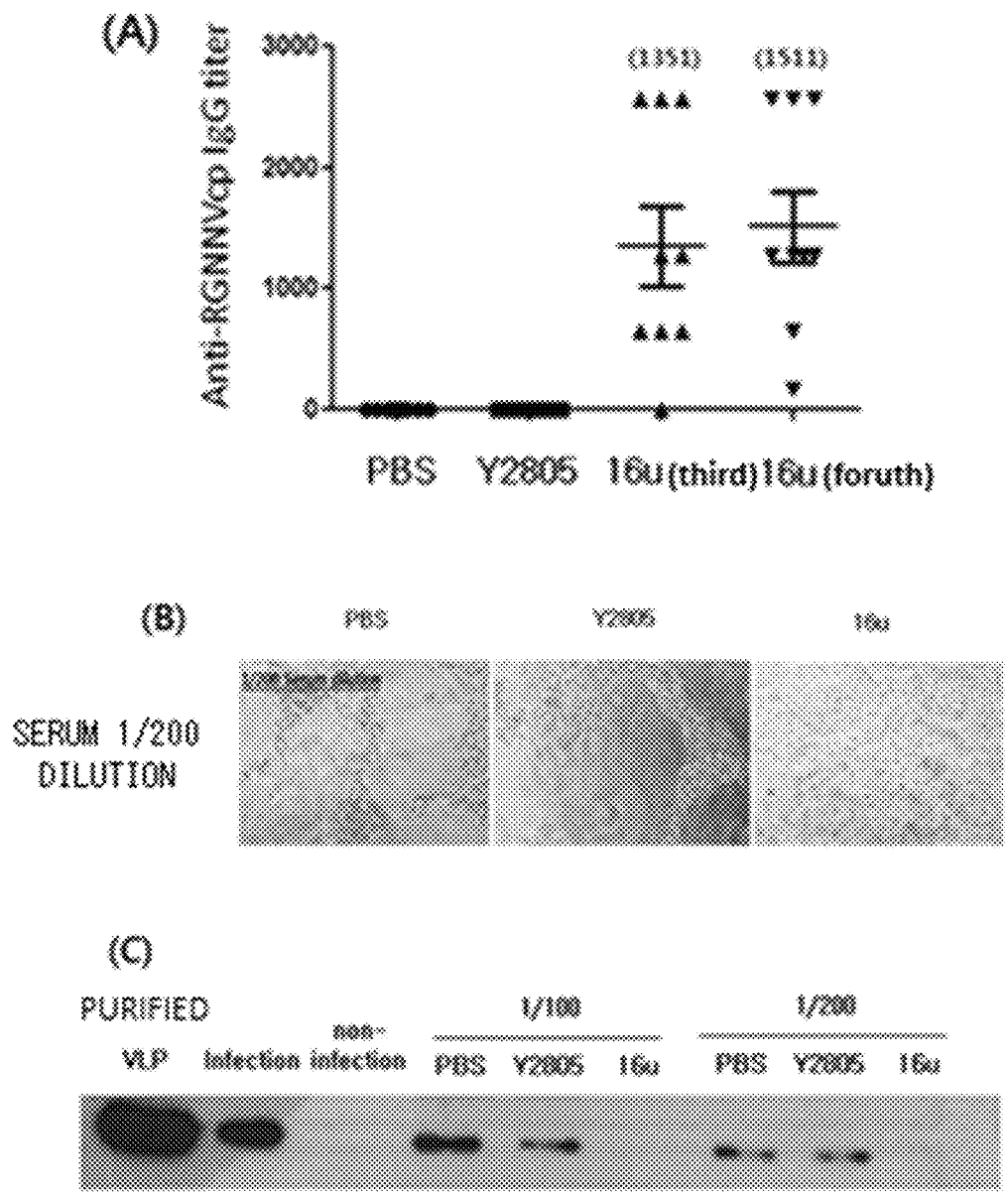

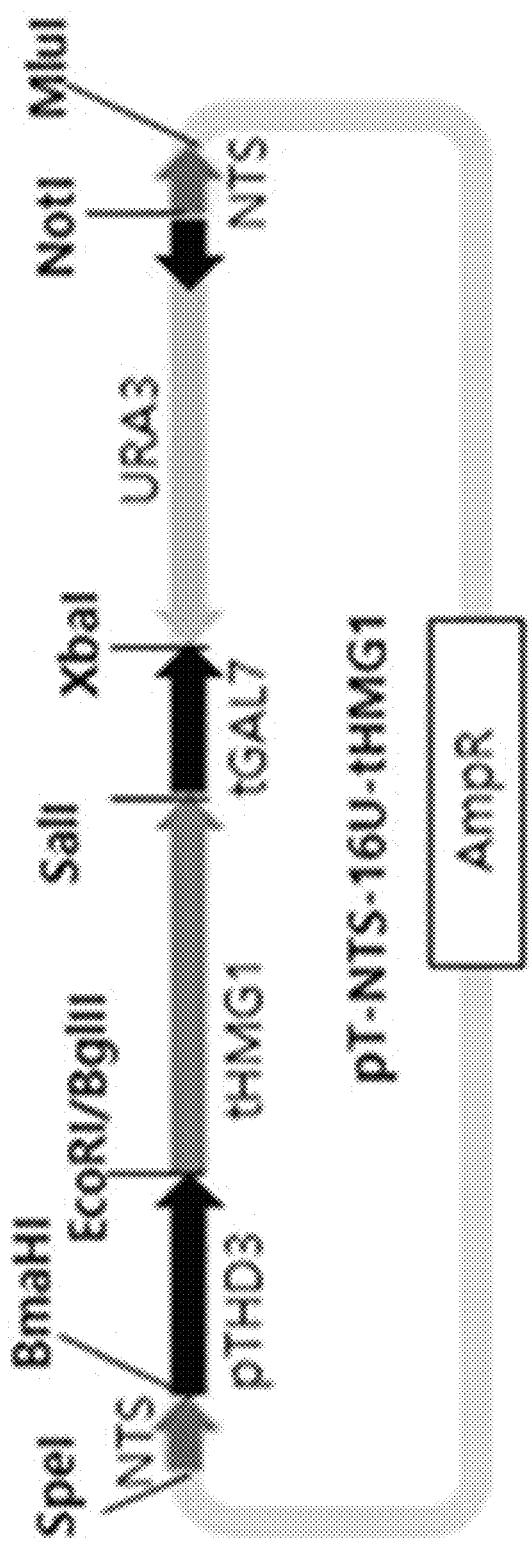
[FIG. 5a]

[FIG. 5b]

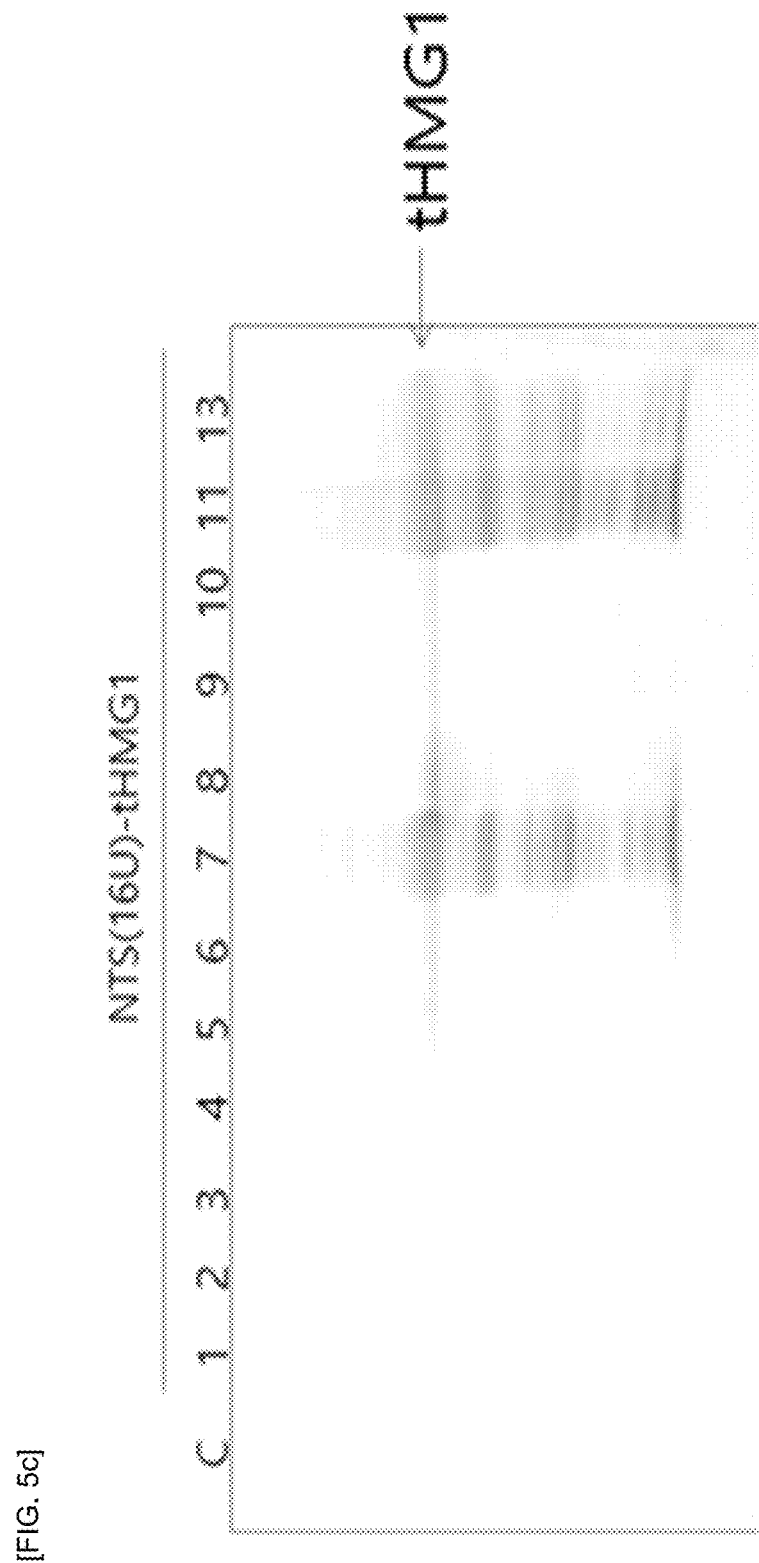
[FIG. 5c]

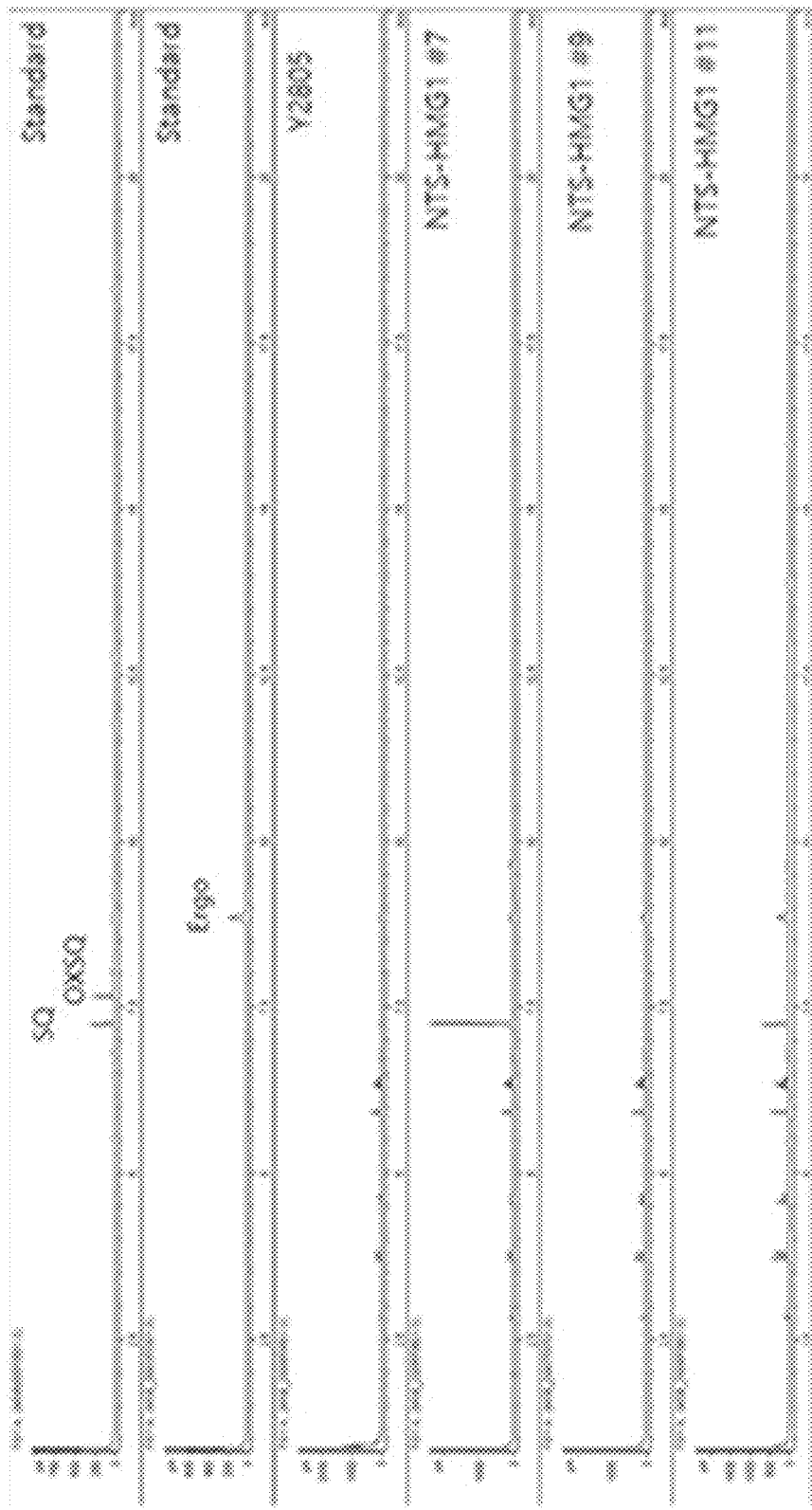
[FIG. 5d]

[FIG. 6a]

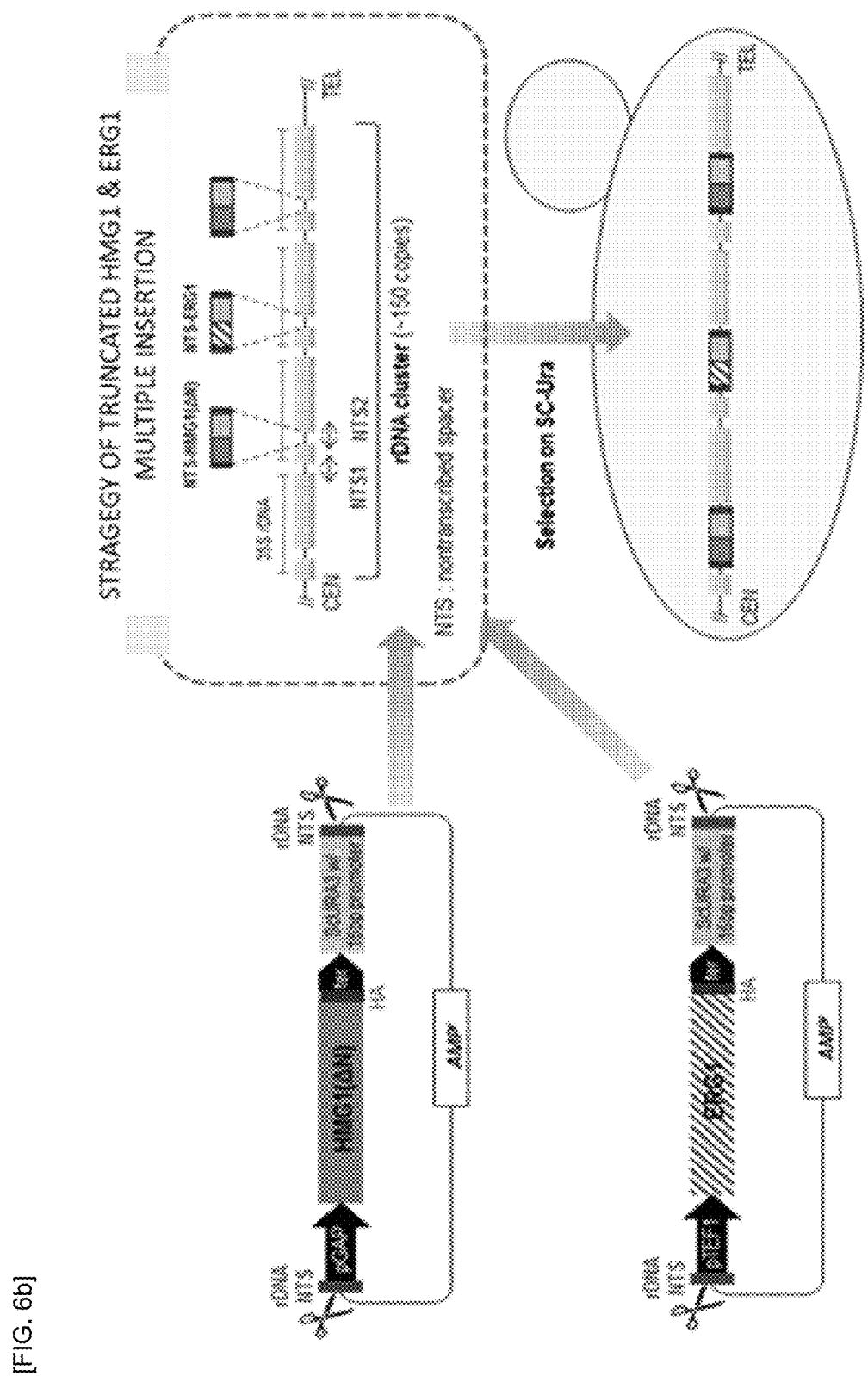
[FIG. 6b]

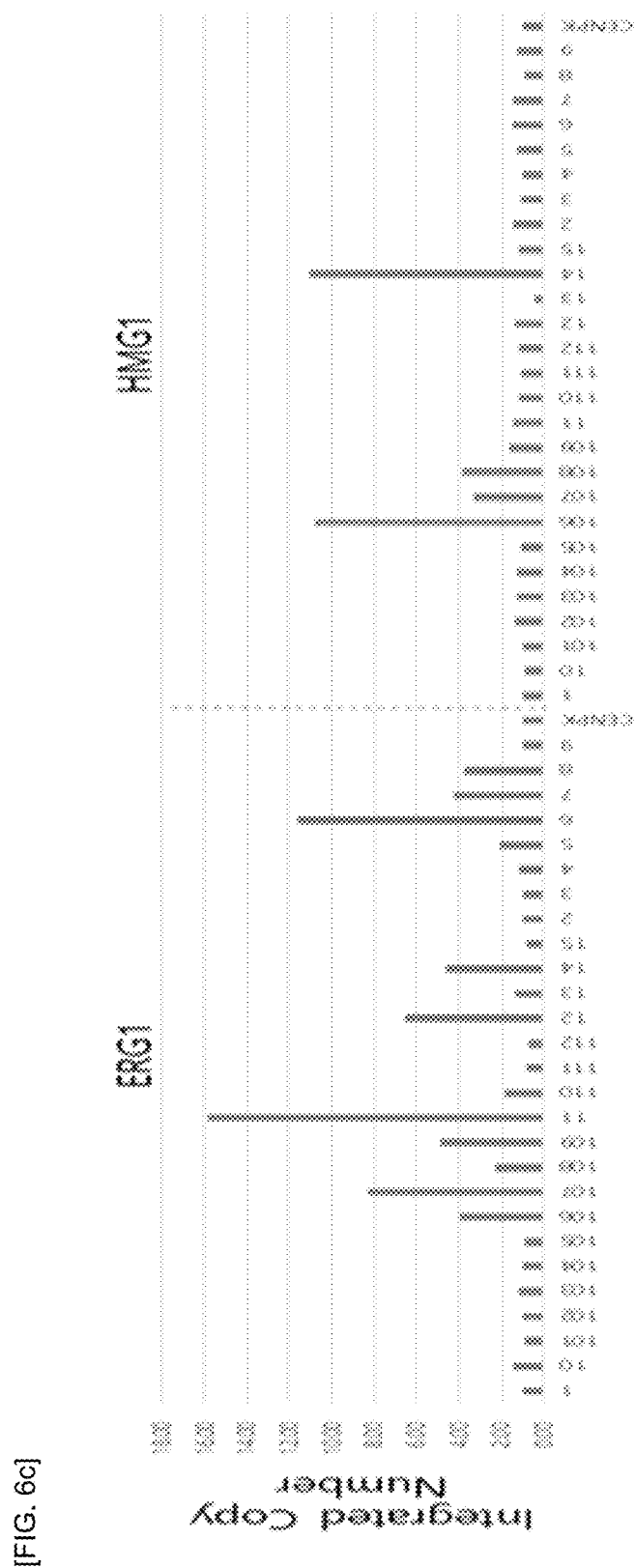
[FIG. 6c]

SEQUENCE LISTING

```
<160> NUMBER OF SEQ ID NOS: 4

<210> SEQ ID NO 1
<211> LENGTH: 47
<212> TYPE: DNA
<213> ORGANISM: Sacchoromyces cerevisiae
```

```
<400> SEQUENCE: 1
cacaagaggt aggtcgaaac agaacatgaa agttggtcgg taggtgc                47

<210> SEQ ID NO 2
<211> LENGTH: 49
<212> TYPE: DNA
<213> ORGANISM: Sacchoromyces cerevisiae

<400> SEQUENCE: 2
ggttttgcac catatcttca taacctgtca ccttgaaact acctctggc              49

<210> SEQ ID NO 3
<211> LENGTH: 16
<212> TYPE: DNA
<213> ORGANISM: Sacchoromyces cerevisiae

<400> SEQUENCE: 3
gaaacgaaga taaatc                                                  16

<210> SEQ ID NO 4
<211> LENGTH: 21
<212> TYPE: DNA
<213> ORGANISM: Sacchoromyces cerevisiae

<400> SEQUENCE: 4 ttaccttta catttcagca a                                             21
```

RDNA NTS-BASED GENE MULTIPLE INSERTION CASSETTE SET AND GRAS-GRADE RECOMBINANT YEAST STRAIN

CROSS REFERENCE TO PRIOR APPLICATIONS

This application is a National Stage Application of PCT International Patent Application No. PCT/KR2014/013047 filed on Dec. 30, 2014, under 35 U.S.C. § 371, which claims priority to Korean Patent Application No. 10-2014-0108910 filed on Aug. 21, 2014, which are all hereby incorporated by reference in their entirety.

TECHNICAL FIELD

The present invention relates to a ribosomal DNA non-transcribed spacer (rDNA NTS)-based gene multiple insertion cassette set and a GRAS-grade recombinant yeast strain using the same. In particular, a gene multiple insertion cassette set including rDNA NTS fragments and an auxotrophic selection marker having an incomplete promoter is developed, and a safe oral recombinant strain is prepared by multiple insertion of an optimum number of the developed gene multiple insertion cassette sets into chromosomes of a *Saccharomyces cerevisiae* strain.

BACKGROUND ART

A infectious disease in agriculture and stockbreeding/fisheries industries is one of the most important problems. Due to the enlargement of the industries such as aquaculture industry, the demand for prevention of eco-friendly disease is increasing in the current environment where the risk of infectious diseases is increasing. In particular, the discovery of drug vaccines and new materials for functional foods with increased immunity is the key technology to grow the future agriculture and stockbreeding/fisheries industries. In order to develop such vaccines for agriculture and stockbreeding/fisheries industries or functional food materials, mass production of stable and economical active substances is essential. The development of a microbial oral vaccine against animal diseases using a transgenic microorganism that produces an antigen protein available as a vaccine is not only inexpensive, but also is available for use as being added to animal feed as an oral vaccine. In this regard, it is expected that farmers will be able to increase income and reduce labor force.

Feed additives are non-nutrient supplementary substances that are assorted in small quantities for the purpose of improving productivity, and antibiotics, probiotics, enzymes, organic acids, flavors, sweeteners, antioxidants, various natural substances, and functional substances may be classified as feed additives. In reality, these feed additives are widely used in livestock feed, and when applied properly to animal feed, positive effects thereof may be resulted even in small amounts. The overall market size of the feed additives reaches about 15 trillion Korean Won in Korea, and continues to grow upon population growth, increased meat consumption, and rising grain prices. Types of the feed additives include amino acids, vitamins, growth-promoting antibiotics, minerals, enzymes, organic acids, carotenoid pigments, and preservatives. Many products are produced through a fermentation process, and their proportion is also increasing. Here, the key factor for successful feed additive business includes microbial manipulation technology and application technology of biomass.

*Saccharomyces cerevisiae*, which is a traditional strain, is used for fermentation of beer and bread for a long period of time, and is a generally recognized as safe (GRAS) grade microorganism whose safety to human body is guaranteed. In particular, yeast has protein secretory organelles in addition to gene transcription and translation systems that are very similar to those of higher organisms, and thus it can produce proteins that are activated by post-translational modification. In this regard, *S. cerevisiae* is used as a more useful host system for the mass production of medicinal proteins derived from higher organisms than *Escherichia coli*. In addition, since *S. cerevisiae* is easy to scale-up due to easy cultivation of strains and purification of extracellular secretory proteins, it is a host system useful for the industrial production of food and recombinant pharmaceutical proteins. Recombinant proteins produced using yeast strains have been successfully mass-produced with hormones (insulin, growth hormone, etc), vaccines (hepatitis vaccine, cervical cancer vaccine, etc), albumin, and hirudin.

It has been reported that beta-glucan, which is a cell wall component of yeast, acts as an adjuvant stimulating a toll-like receptor (TLR), which further increases an immune response when administered with an antigen. Afterwards, studies have been attempted to utilize *S. cerevisiae*, which is a traditional strain, as an antigen delivery material for oral vaccines. Recent studies have shown that, when cell wall components of yeast transmit a risk signal related to microbial infection, antigenic proteins of recombinant yeast increase activity of immune-related cells including T-cells via MHC Class I and II pathways by dendritic cells (DCs). Based on such studies, research on the possibility of developing an oral vaccine for human or veterinary use of recombinant yeast expressing an antigenic protein has attracted attention in terms of a good strategy for the development of a next-generation vaccine. In particular, from a number of studies suggest, vaccine development using recombinant yeast strain has been suggested as an effective delivery system that not only serves as an adjuvant to increase the immune response of yeast, but also appropriately targets antigens to the intestinal mucosa of host animals. In this regard, the possibility of yeast as an oral vaccine carrier is suggested.

Meanwhile, yeast is also in the spotlight as a host capable of introducing various secondary metabolite biosynthetic pathways for expression. Secondary metabolites produced by various organisms are main sources of high-value chemical compounds and often have important medicinal properties. In particular, plant metabolites prevent the infection of bacteria, viruses, and fungi through antioxidant or antibiotic functions, and are also useful as therapeutic agents because they are functional materials beneficial to human health. Thus, there is a great demand for mass production technology utilizing microorganisms. Yeast, which has its own limited secondary biosynthetic pathway, does not interfere with or compete with a foreign metabolism introduced through genetic engineering, and above all, yeast is well associated with various omics analysis systems so that it is possible to obtain comprehensive information about the physiological state of a yeast host through transcript and metabolite analysis. In addition, a detailed model regarding metabolism has been developed, and in silico yeast that can predict the behavior of the modified metabolic network has been constructed, thereby making it easier to design and manufacture artificial cells using the yeast. Furthermore, as a single-celled eukaryotic microorganism, yeast is a host suitable for the expression of a foreign enzyme, such as cytochrome P450, which becomes active only when expressed in organelles such as endoplasmic reticulum and mitochondria, and has an advantages of post-translational modification necessary for enzymatic activity derived from plants and animals, compared with a prokaryotic microbial host.

An important tool set for controlling expression of heterologous genes in yeast is a device capable of regulating the copy number of the desired expression cassette. In the case of traditional yeast, 2 micron-based plasmid includes about 5-30 copies per cell, whereas a yeast centromere/autonomously replicating sequence (CEN/ARS)-based plasmid includes a very small number of copies (about 1 copy per cell). A high-copy-number expression vector strongly expresses encoded genes, thereby generating a large burden on cells and causing instability of the expression vector itself. A low-copy-number expression vector provides a more stable expression platform, but can cause a problem with low gene expression levels. When the expression cassette is inserted into a target region on the yeast host chromosome through homologous recombination, the expression vector can be stably maintained even under the condition of no continuous selection pressure. Techniques have been developed to target ribosomal elements, delta elements, and sigma element sequences, which are present in a repetitive copy of the yeast chromosome, for multiple insertion of expression vectors.

The ribosome is composed of ribosomal RNA (rRNA) molecules and ribosomal proteins, and the eukaryotic ribosome has 28S, 16S, and 5S rRNA molecules. The eukaryotic ribosomal DNA (rDNA) is composed of a coding region and a non-coding region. In addition, rDNA is known to have an evolutionarily conserved region, an internal transcribed spacer (ITS) region showing a faster evolutionary rate than other regions, and an intergenic spacer (IGS) region. A transcription unit of the eukaryotic rRNA includes 18S, 5.8S, and 28S rRNAs in the stated order, wherein each of the rDNAs is separated by two ITS regions for the connection. Other transcription units of the eukaryotic rRNA include 5S rRNA, which is surrounded by a nontranscript sequence (NTS) site. In the case of traditional yeast, S. cerevisiae, an rDNA unit thereof is repeatedly inserted 100 to 150 times on chromosome 12. In the case of multiple insertion expression vectors using such multiple rDNA gene sites, antibiotic resistant genes are mainly used as selection markers for multiple insertion of expression cassettes. However, the use of antibiotics can cause major problems in terms of cost and environment issues as the cultivation size increases. In particular, in the case of recombinant yeast strains with antibiotic resistant markers, safety issues that can amplify the emergence of antibiotic resistant bacteria due to leakage of antibiotic resistant marker genes into ecosystem are raised as a major issue when the recombinant yeast strains are developed as oral vaccines or feed additives. Therefore, there is a need for development of an expression cassette capable of inserting a target gene in multiple copies into host chromosomes without insertion of an antibiotic resistant marker.

DETAILED DESCRIPTION OF THE INVENTION

Technical Problem

An object of the present invention is to provide a gene multiple insertion cassette including an N-terminal fragment of S. cerevisiae ribosomal DNA nontranscribed spacer (rDNA NTS), a target insertion gene, an auxotrophic selection marker gene including a promoter region, and a C-terminal fragment of S. cerevisiae rDNA NTS in the stated order.

Another object of the present invention is to provide a generally recognized as safe (GRAS) grade recombinant S. cerevisiae strain having multiple insertion of the multiple insertion cassette into the S. cerevisiae rDNA without antibiotic resistant marker.

Technical Solution

In order to achieve the above objects, the present invention provides a gene multiple insertion cassette including an N-terminal fragment of Sacchoromyces cerevisiae rDNA NTS, a target insertion gene, an auxotrophic selection marker gene including a promoter region, and a C-terminal fragment of S. cerevisiae rDNA NTS in the stated order.

In addition, the present invention provides a recombinant vector including the gene multiple insertion cassette and a recombinant microorganism transformed with the recombinant vector.

In addition, the present invention provides a recombinant S. cerevisiae strain in which the gene multiple insertion cassette is multiple-inserted into the S. cerevisiae rDNA.

In addition, the present invention provides a vaccine composition including, as an active ingredient, the above strain, a culture product thereof, a cell lysate, or nodavirus capsid protein (NNVcp) isolated and purified therefrom.

In addition, the present invention provides a composition for feed addition including, as an active ingredient, the above strain, a culture product thereof, a cell lysate, or squalene or oxidosqualene isolated and purified therefrom.

Advantageous Effects of the Invention

The present invention relates to rDNA NTS-based gene multiple insertion cassette set and a GRAS-grade recombinant yeast strain using the same. In particular, a gene multiple insertion cassette set including rDNA NTS fragments and an auxotrophic selection marker having an incomplete promoter is developed, and a safe oral recombinant strain is prepared by multiple insertion of an optimum number of the developed gene multiple insertion cassette sets into the chromosomes of S. cerevisiae strain without insertion of antibiotic resistant genes. Nodavirus capsid genes are subjected to multiple insertions using the cassette, and the amount of recombinant protein expression is increased in proportion to the number of insertions. In addition, through multiple insertions of squalene precursor biosynthetic genes using the cassette, a recombinant yeast strain with increased squalene production is prepared. Such a yeast strain producing a recombinant protein and a useful metabolite without an antibiotic resistant marker can be used as an oral vaccine or feed additive at an economical price of the products in livestock industry or aquaculture of fishes. In addition, in the case of yeast strains in which different selection markers cannot be used, a recombinant yeast in which several expression cassettes having the same marker are simultaneously multiple-inserted into more than 100 rDNA NTS sites present on the chromosome of the yeast host can be prepared, and furthermore, it is possible to prepare such a recombinant strain undergone multiple insertions at various ratios. Accordingly, a recombinant strain showing an optimal production yield through insertion of several expression cassettes at an optimal insertion rate can be screened.

DESCRIPTION OF THE DRAWINGS

FIG. 1(A) shows a multiple insertion cassette set for *S. cerevisiae*, the cassette including a URA3 selection marker that is expressed by a promoter set having a different length so as to be multiple-inserted at various numbers into rDNA NTS sites; FIG. 1 (B) shows a schematic diagram showing a multiple insertion strategy; and FIG. 1 (C) shows qRT-PCR analysis results on multiple insertions of the gene encoding nodavirus capsid protein into the rDNA NTS site.

FIG. 2(A) shows a schematic diagram of a multiple insertion cassette set for *S. cerevisiae*, the cassette including a LEU2 selection marker that is expressed by a promoter set having a different length so as to be multiple-inserted at various numbers into rDNA NTS sites; and FIG. 2(B) shows qRT-PCR analysis results on multiple insertions of the gene encoding nodavirus capsid protein into the rDNA NTS site.

FIG. 3(A) shows western blot analysis results to confirm expression of a nadavirus capsid protein among NTS-16U-NNV/Y2805 strains carrying multiple insertion of *S. cerevisiae* codon-optimized nodavirus capsid protein gene with a URA3 selectable marker expressed by a 16-bp promoter; and FIG. 3(B) shows stability analysis results on an NTS-16U-NNV expression cassette inserted into a host chromosome, wherein the term "WT" indicates a sample of wild-type *S. cerevisiae* Y2805 strain, and the term "Positive" indicates a sample of a recombinant strain including an YEGa-MCS-opt-RGNNV-CP vector expressing NNV in a 2μ vector.

FIG. 4 shows (A) analysis results of serum antibody formation levels measured with respect to capsid protein of RGNNV through oral administration of a lyophilized recombinant yeast strain into a mouse to analyze immunogenicity and neutralizing antibody induction of the recombinant NTS-16UNNV/Y2805 yeast strain; (B) results obtained by measuring neutralizing activity against RGNNV in mouse serum; and (C) western blot analysis results obtained from cells and culture medium collected after the serum of the mouse group was diluted to 1/100 or 1/200, mixed with RGNNV, infected with E-11 fish cells, and then, cultured, wherein the western blot analysis is performed to detect RGNNV capsid proteins using mouse anti-RGNNV capsid protein serum.

FIG. 5(A) shows a multiple insertion vector NTS(16U)-tHMG1 for the *S. cerevisiae* gene encoding N-terminal truncated HMG1 (tHMG1), using an URA3 selection marker expressed by a 16-bp promoter; FIG. 5(B) shows qRT-PCR analysis results on multiple insertions of tHMG1 to rDNA NTS sites of *S. cerevisiae*; FIG. 5(C) shows western blot analysis results to confirm expression level of the HMG1 protein; and FIG. 5(D) shows strain selection for squalene mass production by gas chromatography (GC).

FIG. 6(A) shows a schematic diagram of a multiple insertion vector NTS(16U)-ERG1 for *S. cerevisiae* squalene epoxidase gene (ERG1) using an URA3 selection marker expressed by a 16-bp promoter; FIG. 6(B) shows a schematic diagram showing a multiple insertion strategy; and FIG. 6(C) shows qRT-PCR analysis results for selection of a recombinant strain in which NTS(16U)-tHMG1 and NTS (16U)-ERG1 expression cassettes are simultaneously multiple-inserted into rDNA NTS sites of *S. cerevisiae*.

BEST MODE

In this regard, the present inventors developed a technique of inserting only a target gene expression cassette using a ribosomal DNA nontranscribed spacer (rDNA NTS) of a yeast host strain without insertion of antibiotic resistant genes thereto. Unlike the conventional high-expression system, the present inventors completed the present invention by constructing an expression system requiring no supply of antibiotics in terms of production of recombinant protein and useful metabolites, when culturing at a high concentration in terms of production of recombinant protein and useful metabolites. A recombinant yeast strain developed by the gene multiple insertion cassette described herein is an antibiotic-independent high-expression system with high stability of expression cassette, and thus is an expression system suitable for industrialization that can be used as an oral vaccine and feed additive.

The present invention provides a gene multiple insertion cassette including: an N-terminal fragment of *S. cerevisiae* rDNA NTS, (NCBI accession no. X00486.1); a target insertion gene; an auxotrophic selection marker gene including a promoter region; and a C-terminal fragment of *S. cerevisiae* rDNA NTS, in the stated order.

Preferably, the N-terminal fragment of *S. cerevisiae* rDNA NTS may be represented by SEQ ID NO: 1, and the C-terminal fragment of *S. cerevisiae* rDNA NTS may be represented by SEQ ID NO: 2.

Preferably, the auxotrophic selection marker gene may an URA3 gene (NCBI accession no. NM_001178836.3) including a promoter region represented by SEQ ID NO: 3 or an LEU2 gene (NCBI accession no. NM_001178665.1) including a promoter region represented by SEQ ID NO: 4, but embodiments are not limited thereto.

Preferably, the target insertion gene may be a nodavirus capsid protein gene (NNVcp, NCBI accession no. CAE55208.2), a HMG-CoA reductase gene (HMG1, NCBI accession no. NM_001182434.1), or a squalene epoxidase gene (ERG1, NCBI accession no. NM_001181304.1), but embodiments are not limited thereto.

The gene multiple insertion cassette of the present invention may include, in addition to expression regulatory elements such as a promoter, a start codon, a stop codon, a polyadenylation signal, and an enhancer, a signal sequence or a leader sequence for membrane targeting or secretion. In addition the gene multiple insertion cassette may be variously prepared according to purposes.

In addition, the present invention provides a recombinant vector including the gene multiple insertion cassette. Preferably, the recombinant vector may have one of cleavage maps selected from the group consisting of FIGS. 1(A), 2(A), 5(A), and 6(A), but embodiments are not limited thereto.

The term "vector" as used herein refers to a DNA molecule with autonomous replication capability used to carry a clone gene (or another piece of a DNA clone).

In addition, the present invention provides a recombinant microorganism transformed with the recombinant vector. Preferably, the recombinant microorganism may be *Escherichia coli*, but embodiments are not limited thereto.

More preferably, the recombinant microorganism may be NTS-16U-NNV (Accession No: KCTC 12608BP), NTS-50L-NNV (Accession No: KCTC 12610BP), NTS-16U-tHMG1 (Accession No: KCTC 12609BP), or NTS-16U-ERG1 (Accession No: KCTC 12607BP).

The NTS-16U-NNV (Accession No: KCTC 12608BP) strain may be an *E. coli* strain transformed with a pT-NTS-16U-NNV of FIG. 1(A) of the present specification.

The NTS-50L-NNV (Accession No: KCTC 12610BP) strain may be an *E. coli* strain transformed with a pT-NTS-50L-NNV of FIG. 2(A) of the present specification.

The NTS-16U-tHMG1 (Accession No: KCTC 12609BP) strain may be an *E. coli* strain transformed with a pT-NTS-16U-tHMG1 of FIG. 5(A) of the present specification.

The NTS-16U-ERG1 (Accession No: KCTC 12607BP) strain may be an *E. coli* strain transformed with a pT-NTS-16U-ERG1 of FIG. 6(A) of the present specification.

In addition, the present invention provides a recombinant *S. cerevisiae* strain in which the gene multiple insertion cassette is multiple-inserted into *S. cerevisiae* rDNA.

Preferably, the strain may be a recombinant *S. cerevisiae* Y2805/NTS-16U-NNV strain (Accession No: KCTC 12611BP) or a recombinant *S. cerevisiae* Y2806/NTS-50L-NNV strain (Accession No: KCTC 12613BP), wherein each of the strains includes a nodavirus capsid protein gene (NNV) multiple-inserted thereto.

Preferably, the strain may be a recombinant *S. cerevisiae* Y2805/NTS-16U-tHMG strain (Accession No: KCTC 12612BP), wherein the strain includes a HMG-CoA reductase gene (HMG1) multiple-inserted thereto.

Preferably, the strain may be a recombinant *S. cerevisiae* CEN.PK-1C/NTS-16U-tHMG & NTS-16U-ERG1 strain, wherein the strain includes HMG1 and a squalene epoxidase gene (ERG1) multiple-inserted thereto.

In addition, the present invention provides a vaccine composition including, as an active ingredient, the above strain, a culture product thereof, a cell lysate, or a nodavirus capsid protein (NNV) isolated and purified therefrom.

The vaccine composition of the present invention may include a pharmaceutically acceptable carrier, which is a component suitable for delivering an antigenic substance to in vivo sites. Examples of the pharmaceutically acceptable carrier may include water, saline solution, phosphate buffered saline solution, Ringer's, dextrose solution, serum-containing solution, Hans's solution, other water-soluble physiological equilibrium solution, oils, esters, and glycols, but are not limited thereto.

The carrier may include a suitable auxiliary ingredient and a preservative to enhance chemical stability and isotacticity, and may also include a stabilizer such as Trehalose, glycin, sorbitol, lactose, or monosodium glutamate (MSG) to protect the vaccine composition against temperature changes or lyophilization. The vaccine composition of the present invention may include suspension liquid such as sterile water or saline solution (preferably, buffered saline solution).

The vaccine composition of the present invention may include an adjuvant in a sufficient amount to enhance an immune response to an immunogen. For example, the vaccine composition of the present invention may include an aluminum salt (aluminum phosphate or aluminum hydroxide), a squalene mixture (SAF-1), a muramyl peptide, a saponin derivative, a cell wall product of mycobacteria, monophosphoryl lipid A, a mycolic acid derivative, a non-ionic block copolymer surfactant, Quil A, a cholera toxin B subunit, polyphosphazene and a derivative thereof, and an immunostimulating complex (ISCOM), but embodiments are not limited thereto.

As with all other vaccine compositions, an immunologically effective dose of the immunogen should be determined empirically, and factors considered in this case may include immunogenicity, administration routes, and the number of administration of immunogens to be administered.

The culture of cells or the nodavirus capsid protein, which is an antigenic substance in the vaccine composition of the present invention, may be present at various concentrations in the vaccine composition of the present invention. However, in general, such an antigenic substance may be present at a concentration necessary to induce antibody formation at an appropriate level in the human body.

The vaccine composition of the present invention may be used to protect or treat animals susceptible to nodavirus infection by administration via the whole body or mucosal route. The administration of the vaccine composition may include, intramuscular, intraperitoneal, intradermal, or subcutaneous injection, oral administration/meal, respiratory organs, or mucosal administration to the urogenital tract, but embodiments are not limited thereto.

In addition, the present invention provides a composition for feed addition including, as an active ingredient, the above strain, a culture product thereof, a cell lysate, or squalene or oxidosqualene isolated and purified therefrom.

The feed may be constituted by adding the composition for feed additive of the present invention to a feed of a known constitution commonly used for livestock breeding.

The feed of the known constitution may include all commercially available feeds, and examples thereof include rice bran, corn, soybean meal, bean, sorghum, rice, barley, wheat, oats, rye, millet, buckwheat, triticale, sweet potato, tapioca, wheat bran, barley bran, soybean pod, corn bran, malt sprouts, starch pulp, coffee ground, silkworm excreta, kelp meal, cotton seed meal, rapeseed oil meal, canola meal, perilla meal, sesame oil meal, linseed oil meal, sunflower seed oil meal, peanut meal, coconut meal, corn gluten, distillers dried grains, corn germ meal, red-pepper seed meal, lupin seed, fish meal, feather meal, and meat meal.

In addition, the composition may include typical feed additives such as salts, and feed additives for special purposes, such as bone meals, calcium phosphates, mineral compounds, vitamins, amino acids, antibiotics, and hormones.

The composition for feed addition of the present invention including, as an active ingredient, the above strain, a culture product thereof, a cell lysate, or squalene or oxidosqualene isolated and purified therefrom, may be administered to livestock or poultry in an amount of 0.5 g/kg to 1.0 g/kg per day. Here, such an amount may be suitably adjusted by one of ordinary skill in the art depending on the type of animal to be administered, the age of the animal, the weight of the animal, the disease of the animal to be prevented, and the desired effect.

Furthermore, the prevent invention provides a technique of preparing a GRAS-grade recombinant yeast strain for mass production of various recombinant proteins or useful metabolites in addition to the nodavirus capsid protein and squalene. That is, such a technique may be used to prepare a recombinant yeast strain that mass-expresses proteins derived from infectious viruses that cause infections in fish, livestock, and humans, such as iridovirus, foot-and-mouth disease virus, porcine epidemic diarrhea virus, and hepatitis B virus, and from infectious bacteria such as swine enzootic pneumonia. In addition, such a technique may be used to prepare a recombinant yeast strain that mass-produces various isoprenoid-based high-functional metabolites, such as artemisinin and ginsenoside, or secondary metabolites of polyphenolic compounds having antioxidant properties, such as flavonoid and anthocyanin.

MODE OF THE INVENTION

Hereinafter, the present invention will be described in further detail with reference to the following examples. These examples are for illustrative purposes only, and it will be understood by one of ordinary skill in the art that these examples are not intended to limit the scope of the present invention.

Example 1: Preparation of Selection Marker Having Promoter of Various Lengths and Development of rDNA NTS-Targeting Multiple Insertion Vector Set Using the Selection Marker To construct a gene multiple insertion cassette using *S. cerevisiae* as a host for production of an oral recombinant protein, an N-terminal fragment (47 bp) and a C-terminal fragment (49 bp) of rDNA NTS were each fused to the ScURA3 selection marker gene by PCR using a primer set of NTS-16U-fw and NTS-16U-rv that was designed as the primer for amplification of the URA3 gene with a 16-bp promoter (16U). The amplified fragment was inserted into a pGEM T easy vector system, thereby preparing a pT-NTS-16U vector. Afterwards, a GAL10(p)-NNV-GAL7(t) fragment was amplified using YEGa-MCS-NNVcp (disclosed according to WO2014046410 A1) as a template and a primer set of GAL10P-fw and GAL7T-rv, and then, the amplified fragment was treated with BamHI/XbaI to be inserted into pT-NTS-16U, thereby finally preparing a pT-NTS-16U-NNV vector (FIG. 1A). The pT-NTS-16U-NNV vector was treated with NotI/XbaI to remove the 16U gene, and then, a primer set of 77U-fw and 77U-rv was used to synthesize the URA3 gene having a 77-bp promoter (77U) while a primer set of 300U-fw and 300U-rv was used to synthesize the URA3 gene having a 300-bp promoter (300U). Then, the synthesized fragments were each inserted into a backbone vector prepared by treatment of NotI/XbaI, thereby constructing a pT-NTS-77U-NNV vector and a pT-NTS-300U-NNV vector (FIG. 1A). Each of these vectors was treated with SphI/MlnI to collect the expression cassette therefrom. After *S. cerevisiae* Y2805 (MATa pep4::HSI3, prb1-d, can1, GAL2, his3, ura3-52) strain was transformed, transformants surviving in SC minimal medium that was deficient in uracil (SC-URA) were selected, so as to induce multiple insertions of the expression cassette into the NTS sites on the host rRNA. Following pre-incubation of the harvested Ura+ transformants, the transformants were inoculated at OD=0.5, cultured for 24 hours, and then, subjected to centrifugation to collect yeast cells. To the collected yeast cells, STES buffer solution (20 mM Tris-HCl pH 7.5, 500 mM NaCl, 10 mM EDTA, and 1% SDS) and glass beads were added by the same amount to allow cell disruption, and then, 200 μl of TE buffer solution (10 mM Tris-HCl pH 8.0 and 1 mM EDTA) and 200 μl of mixed solution of phenol/chloroform/iso-amyalcohol (at a ratio of 24:1:1) were added thereto to allow another cell disruption. Cell lysates were harvested, and then, genomic DNA (gDNA) thereof was collected using the ethanol precipitation method. The collected gDNA was subjected to quantatitive real-time polymerase chain reaction (qRT-PCR) using the primers for URA3 RT-PCR, URA3RT-fw and URA3RT-rv (Table 1) (FIG. 1C). Interestingly, compared to the transformants to which the NTS-300U-NNV cassette was inserted, the transformants obtained using the two vectors NTS-77U-NNV and NTS-16U-NNV showed a greater number of cassette insertions. In particular, compared to the recombinant transformed with the NTS-77U-NNV cassette, the recombinant transformed with the NTS-16U-NNV cassette showed a large number of insertions on average (FIG. 1C).

Regarding a *S. cerevisiae* LEU2 market set, in the same manner, pT-NTS-400L-NNV, pT-NTS-100L-NNV, and pT-NTS-50L-NNV vectors were prepared in a way that the promoter length was changed to 50-bp, 100-bp, and 400-bp, respectively, and a fragment of XbaI/NotI ScURA3 marker gene was replaced (FIG. 2A). Each of the prepared vectors was treated with SphI/MlnI to collect the expression cassette therefrom. After *S. cerevisiae* Y2806 (MATa pep4::HSI3, prb1-d, can1, GAL2, his3, ura3-52, leu2::tc) strain was transformed, transformants surviving in SC minimal medium that was deficient in leucine (SC-LEU) were selected, so as to induce multiple insertions of the expression cassette into the NTS sites on the host rRNA. In the case of the NTS-50/100/400L-NNV vectors, only the recombinant strain to which the NTS-50L-NNV cassette was inserted showed multiple insertions, wherein the insertions were made up to about 50 copies (FIG. 2B). The prepared multiple insertion cassette was also available for use in a BY4742 strain other than the *S. cerevisiae* Y2805 strain. In this regard, it is expected that the multiple insertion cassette prepared in the present invention will be usable in several *S. cerevisiae* strains.

TABLE 1

| Gene | Primer | Base sequence |
|---|---|---|
| HMG1 | tHMG1-fw | 5'-GGAATTCATGCCAGTTT TAACCAATAA-3' |
|  | HMG1-rv | 5'-GCGTCGACTTACGCATA GTCAGGAACATCGTATGGGT AGGATTTAATGCAGGTGACG G-3' |
| ERG1 | ERG1-fw | 5'-AACTGCAGATGTCTGCT GTTAACGTTGC-3' |
|  | ERG1-rv | 5'-GCGTCGACTTACGCATA GTCAGGAACATCGTATGGGT AACCAATCAACTCACCAAA C-3' |
| GAL10/ GAL7 | GAL10P-fw | 5'-CGGGATCCATCGCTTCG CTGATTAATTA-3' |
|  | GAL7T-rv | 5'-GCTCTAGAGGGGAAACT TAAAGAAATTC-3' |
| TEF1 | TEF1P-fw | 5'-CGGGATCCAGCTCATAG CTTCAAAATGTTTC-3' |
|  | TEF1P-rv | 5'-AACTGCAGCTAGAAAAC TTAGATTAGATTGC-3' |
| TDH3 | GAPDHP-fw | 5'-CGGGATCCGGTAGAATC ATTTTG-3' |
|  | GAPDHP-rv | 5'-GGAATTCTGTTTATGTG TGTTTATTCG-3' |
| LEU2 | LEU2RT-fw | 5'-TCTCCGATGAAGCCTCC GTT-3' |
|  | LEU2RT-rv | 5'-ACCGTGGCATGGTTCGT ACA-3' |
|  | 400L-fw | 5'-GCTCTAGAGCTGGCGTA ATAGCGAAGAG-3' |
|  | 400L-rv | 5'-ATAAGAATGCGGCCGCG GAATACTCAGGTATCGTAAG A-3' |
|  | 50L-rv | 5'-ATAAGAATGCGGCCGCC TTACCTTTTACATTTCAGCA A-3' |
|  | 100L-rv | 5'-ATAAGAATGCGGCCGCC CAATAGGTGGTTAGCAATC G-3' |
| URA3 | URA3RT-fw | 5'-AGAATTGTCATGCAAGG GCTCC-3' |
|  | URA3RT-rv | 5'-TCCACCCATGTCTCTTT GAGCA-3' |
|  | 300U-fw | 5'-GCTCTAGAGGGTAATAA CTGATATAATT-3' |
|  | 300U-rv | 5'-ATAAGAATGCGGCCGCT TCAATTCATCATTTTTTTTT T-3' |
|  | 77U-rv | 5'-ATAAGAATGCGGCCGCT AGTGTTGAAGAAACATGA A-3' |

TABLE 1-continued

| Gene | Primer | Base sequence |
|---|---|---|
| | 16U-rv | 5'-ATAAGAATGCGGCCGCG AAACGAAGATAAATCATGTC G-3' |
| rDNA NTS | NTS-16U-fw | 5'-CATGCATGCCACAAGAG GTAGGTCGAAACAGAACATG AAAGTTGGTCGGTAGGTGCG GATCCGCTCTAGAGGGTAAT AACTGATATAATT-3' |
| | NTS-16U-rv | 5'-CGACGCGTGGTTTTGCA CCATATCTTCATAACCTGTC ACCTTGAAACTACCTCTGGC GCGGCCGCGAAACGAAGATA AATCATGT-3' |

[1]Restriction enzymes are marked with an underline.
[2]NTS sites are shown in bold letters.
[3]HA taq sites are shown in italicized letters.

Example 2: Development of Recombinant Yeast Capable of Mass-Producing Oral Nadavirus Vaccine Using pT-NTS-16U-NNV, and Characterization Analysis Thereon To confirm the expression amount of nodavirus capsid proteins in the Y2805/NTS-16U-NNV strains obtained in Example 1, the yeast cells were collected, and then, TNE buffer solution (50 mM Tris-HCl pH 7.5, 150 mM NaCl, 5 mM EDTA) was added thereto to allow cell disruption, thereby preparing cell lysates. The cell lysates were mixed with SDS sample-loading buffer solution (62.5 mM Tris-HCl pH 6.8, 0.1% BPB, 10% glycerol, 10% SDS, and 1% beta-mercaptoethanol), and then, heat-treated in boiling water for 10 minutes, and the western blot analysis was performed thereon. Here, a nodavirus capsid antibody was used as a primary antibody, and rabbit-alkalion phosphatase (AP) was used as a secondary antibody. As a result, it was confirmed that the nodavirus capsid protein having an expected size was expressed in the yeast strain to which the NNV expression cassette was multiple-inserted. In addition, it was also confirmed that the number of the inserted cassettes and the level of the protein expression were increased in a direct proportional manner (FIG. 3A). In the western blot analysis, the term "WT" indicates a sample of wild-type *S. cerevisiae* Y2805 strain, and the term "Positive" indicates a sample of the recombinant strain including the YEGa-MCS-opt-RGNNV-CP vector expressing NNV capsid protein (NNVcp) under the control of a GAL10 promoter in a 2μ vector prepared according to the previous study of the present research team members. Referring to the results of FIG. 3, it was confirmed that the recombinant yeast strains in which only the NVVcp expression cassette was inserted into the NTS sites on rDNA using the pT-NTS-16U-NNV showed NVV expression at the almost same level as or at a slightly higher level than the existing recombinant yeast strain.

For comparative analysis regarding stability between the previously studied YEGa-MCS-NNVcp/Y2805 (positive control(+)) strain and the NTS-16U-NNV/Y2805 strain prepared in the present invention, qRT-PCR analysis was performed on samples cultured for 24, 48, and 72 hours in YPG nutrient medium and SC-URA-Gal selective medium (FIG. 3B). As a result, it was confirmed that the YEGα-MCS-NNVcp/Y2805 (positive control(+)) strain stably maintain the number of insertions in the SC-URA-Gal selective medium, whereas the YPG nutrient medium was found to lose a large number of vectors by 24-hour culture only. However, in the case of the NTS-16U-NNV/Y2805 strain, regardless of the YPG nutrient medium and the Sc-URA-Gal selective medium, it was confirmed that a large number of the cassettes were stably maintained (FIG. 3B).

To verify the possibility that the recombinant yeast strain prepared with the gene multiple insertion cassette developed in the present invention can be developed as an oral vaccine, immunogenicity and neutralizing antibody induction assay of the NTS-16UNNV/Y2805 yeast strain were performed. The recombinant NTS-16U-NNV/Y2805 cells lyophilized after being cultured in the YPG medium for 72 hours were orally administered to mice, and then, the level of serum antibody formation with respect to the RGNNV capsid protein was analyzed according to the ELISA method (FIG. 4A). Here, as a negative control, a wild-type Y2805 strain lyophilized with phosphate-buffered saline (PBS) was subjected to oral immunization. As a result of measuring the antibody titer levels with respect to the serum RGNNV capsid protein after the recombinant NTS-16UNNV/Y2805 cells were orally administered to mice 3 times and 4 times, it was confirmed that the formation of antibodies recognizing nodavirus capsid protein in the mice to which the recombinant NTS-16UNNV/Y2805 yeast cells were orally inserted was significantly induced, compared to the negative control group. In addition, to measure the neutralizing activity against the nodavirus RGNNV, E-11 fish cells cultured in a single layer were infected with a mixed solution of RGNNV and mouse serum harvested after the 4$^{th}$ oral immunization, and then, neutralizing activity of the cultured cells was observed through the presence of cell lesion (FIG. 4B). Here, the serum was diluted to 1/200, and then, mixed with RGNNV to infect the cells. In the mouse serum in which the wild-type Y2805 strain lyophilized with PBS was subjected to oral immunization, it was confirmed that the RGNNV was not neutralized while cell lesions appeared. However, in the mouse serum in which the recombinant NTS-16U-NNV/Y2805 yeast cells were subjected to oral immunization, cell lesions did not appear, meaning that the RGNNV was successfully neutralized. Furthermore, as a resulting of performing the western blot analysis on the whole collection of cells and culture medium collected after the mouse serum was diluted to 1/100 or 1/200, mixed with RGNNV, infected with E-11 fish cells, and then, cultured, it was confirmed that RGNNV capsid proteins were strongly detected in the cells applied with PBS and the serum of Y2805 group while RGNNV capsid proteins were not detected in the cells applied with the serum of the NTS-16U-NNV/Y2805 group. That is, it was confirmed that the oral immunization of the NTS-16U-NNV/Y2805 group induced neutralizing antibodies against RGNNV. Based on the results, the recombinant nodavirus capsid expression yeast strain prepared with the gene multiple insertion cassette developed in the present invention strongly suggests the possibility of being developed as an oral vaccine.

Example 3: Preparation of Recombinant Yeast Strain for Mass Production of Squalene Using Multiple Insertion Vector Using Essential Amino Acid Selection Marker Having rDNA NTS and Incomplete Promoter To prepare a recombinant *S. cerevisiae* strain for mass production of squalene, a BamHI/SalI GAL10(p)-NNV gene fragment was removed from the prepared pT-NTS-16U-NNV vector, and then, the HMG1 gene from which 552 N-terminal amino acids were removed (tHMG1) was amplified thereon using a primer set of tHMG1-fw and tHMG1-rv of Table 1. The amplified gene was connected with a TDH3 promoter for the insertion of the prepared TDH3(p)-tHMG1 gene fragment, thereby preparing a pT-NTS-16U-tHMG1 vector (FIG. 5A). Then, the prepared pT-NTS-16U-tHMG1 vector was cleaved by SpeI and MluI so that the NTS-16U-tHMG1 cassette was collected therefrom, and then, it was introduced to the *S. cerevisiae* Y2805 strain. The URA3 marker gene was used to select transformants surviving in the SC-URA medium. Regarding the Y2805/NTS-16U-tHMG1 strain which is the obtained transformant, gDNA thereof was collected in the same manner. The collected gDNA was subjected to qRT-PCR using primers for URA3 RT-PCR, and then, confirmed by the western blot analysis. As a result, recombinant strains to which various cassettes were inserted were obtained (FIGS. 5B and 5C).

Squalene, which is expected to increase production thereof due to overexpression of tHMG1 gene on a HMG-CoA reductase from which 552 N-terminal amino acids were removed, was confirmed by gas chromatochraphy (GC) analysis. After days from the start of the main culture of the obtained transformant, Y2805/NTS-16U-tHMG1 strain, in the YPD medium with $OD_{600}$ (0.5), a sample thereof was collected. 100 μl of 50 mM Tris-HCl (pH 7.5) was added 0.01 g (50 μl) of yeast cells in the same amount, and then, a beadbeater (5000, 10 s, 3 times) was used to allow cell disruption. The supernatant was collected by centrifugation, and hexane of the same volume was added thereto, thereby obtaining another supernatant (i.e., hexane layer) by centrifugation. To remove moisture remaining in the obtained hexane layer, $Na_2SO_4$ powder was added thereto, the supernatant (i.e., a hexane layer) was collected again through centrifugation, hexane was removed by drying, and then, the sample was re-dissolved in 150 μl of chloroform, followed by GC analysis. As a result, it was confirmed that a high amount of squalene was produced in the recombinant strain No. 7 to which about 4 cassettes were inserted (FIG. 5D). Unlike the production of recombinant proteins, squalene production did not increase proportionally with the number of insertions, but qRT-PCR screen provided information on the number of insertions suitable for mass production of squalene.

Example 4: Simultaneous Multiple Insertion of Two Types of Vectors with the Same Selection Markers Using Auxotrophic Selection Marker Having rDNA NTS and Incomplete Promoter in *S. Cerevisiae*

By utilizing the advantage that the present gene multiple insertion vector can be inserted into rDNA NTS with high efficiency up to 50 copies by using a selection marker gene having a short promoter, the construction of a recombinant yeast strain to which two types of vectors with the same selection markers are simultaneously inserted has been attempted. For example, it is attempted that the NTS-16U-tHMG1 cassette (containing *S. cerevisiae* HMG-CoA reductase gene with a truncated N-terminal; tHMG1) and the NTS-16U-ERG1 cassette (containing *S. cerevisiae* squalene epoxidase gene; ERG1) were simultaneously inserted to prepare a recombinant strain for mass production of oxidosqualene (FIG. 6A). To prepare the NTS-16U-ERG1 cassette, the BamHI/SalI GAL10(p)-NNV fragment was removed from the pT-NTS-16U-NNV vector, and then, the BamHI/SalI TEF(p)-ERG1 gene fragment, which was prepared by connecting the TEF1 promoter and the ERG1 gene that were amplified by PCR using the primers of Table 1, was inserted thereto, thereby preparing a pT-NTS-16U-ERG1 vector. The two cassettes, i.e., NTS-16U-tHMG1 and NTS-16U-ERG1, were each cleaved by SpeI/MluI, collected, and then, introduced into *S. cerevisiae* CEN. PK-1C (MATa ura3-52 trp1-289 leu2-3,112 his3-D1 MAL2-8C SUC2). Then, transformant surviving in the SC-URA minimal medium were selected (FIG. 6B). Regarding the the CEN.PK-1C/NTS-16U-tHMG1/NTS-16U-ERG1 strain which is the harvested transformant, gDNA thereof was collected in the same manner. The collected gDNA was subjected to qRT-PCR using primers for HMG1, ERG1 RT-PCR. As a result, the transformants #106(4:1), #107(8:3), #108(2:4), #109(5:2), and #14(5:11), to which the ERG1 expression cassette was multiple-inserted simultaneously along with the tHMG1 expression cassette at various ratios, were obtained.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

The recombinant microorganisms, NTS-16U-NNV (Accession No: KCTC 12608BP, Date of Deposit: Jun. 25, 2014), NTS-50L-NNV (Accession No: KCTC 12610BP, Date of Deposit: Jun. 25, 2014), NTS-16U-tHMG1 (Accession No: KCTC 12609BP, Date of Deposit: Jun. 25, 2014), and NTS-16U-ERG1 (Accession No: KCTC 12607BP, Date of Deposit: Jun. 25, 2014), are deposited with the Korean Collection for Type Cultures (KCTC).

The strains, *S. cerevisiae* Y2805/NTS-16U-NNV (Accession No: KCTC 12611BP, Date of Deposit: Jun. 25, 2014), *S. cerevisiae* Y2806/NTS-50L-NNV (Accession No: KCTC 12613BP, Date of Deposit: Jun. 25, 2014), and *S. cerevisiae* Y2805/NTS-16U-tHMG strain (Accession No: KCTC 12612BP, Date of Deposit: Jun. 25, 2014), are deposited with the Korean Collection for Type Cultures (KCTC).

The address of the KCTC is 125 Gwahak-ro, Yuseong-gu, Daejeon 305-806, Republic of Korea.

The invention claimed is:

1. A gene multiple insertion cassette comprising:
   a 5'-end fragment of *Sacchoromyces cerevisiae* ribosomal DNA nontranscribed spacer (rDNA NTS) consisting of SEP ID NO: 1;
   a target insertion gene;
   an auxotrophic selection marker gene comprising a promoter region; and
   a 3'-end fragment of *S. cerevisiae* rDNA NTS consisting of SEP ID NO: 2, in the stated order.

2. The gene multiple insertion cassette of claim 1, wherein the auxotrophic selection marker gene is a URA3 gene comprising a promoter region consisting of SEQ ID NO: 3 or a LEU2 gene comprising a promoter region consisting of SEQ ID NO: 4.

3. The gene multiple insertion cassette of claim 1, wherein the target insertion gene is a nodavirus capsid protein gene (NNV), an HMG-CoA reductase gene (HMG1), or a squalene epoxidase gene (ERG1).

4. A recombinant vector comprising the gene multiple insertion cassette of claim 1.

5. The recombinant vector of claim 4, wherein the recombinant vector has a restriction map selected from the group consisting of FIGS. 1(A), 2(A), 5(A), and 6(A).

6. A recombinant microorganism transformed with the recombinant vector of claim 4.

7. The recombinant microorganism of claim 6, wherein the recombinant microorganism is *Escherichia coli*.

8. The recombinant microorganism of claim 7, wherein the recombinant microorganism is one selected from NTS-16U-NNV (Accession No: KCTC 12608BP), NTS-50L-NNV (Accession No: KCTC 126108P), NTS-16U-tHMGI (Accession No: KCTC 12609BP), and NTS-16U-ERG1 (Accession No: KCTC 12607BP).

9. A recombinant *Saccharomyces cerevisiae* strain in which the gene multiple insertion cassette of claim 1 is multiply-inserted into *S. cerevisiae* ribosomal DNA (rDNA).

10. The recombinant *S. cerevisiae* strain of claim 9, wherein the strain is a recombinant *S. cerevisiae* Y2805/NTS-16U-NNV strain (Accession No: KCTC 1261 IBP) or a recombinant *S. cerevisiae* Y2806/NTS-50L-NNV strain (Accession No: KCTC 12613BP), wherein each of the strains comprises a nodavirus capsid protein gene (NNVcp) multiply-inserted therein.

11. The recombinant *S. cerevisiae* strain of claim 9, wherein the strain is a recombinant *S. cerevisiae* Y2805/NTS-16U-tHMG strain (Accession No: KCTC 12612BP), wherein the strain comprises a HMG-CoA reductase gene (HMG1) multiply-inserted therein.

12. The recombinant *S. cerevisiae* strain of claim 9, wherein the strain is a recombinant *S. cerevisiae* CEN.PK-1 C/NTS-16U-tHMG/NTS-16U-ERGI strain, wherein the strain comprises HMG1 and a squalene epoxidase gene (ERG1) multiply-inserted therein.

13. A method of making a vaccine for livestock, comprising:
   preparing a composition comprising, as an active ingredient, a strain of claim 10, a culture product thereof, a cell lysate, or a nodavirus capsid protein (NNVcp) isolated and purified therefrom; and
   administering the vaccine having the composition to the livestock.

14. The method of claim 13, wherein the vaccine is an oral vaccine.

15. A method of making teed additive for livestock, comprising:
   preparing a composition comprising, as an active ingredient, the strain of claim 11, a culture product thereof, a cell lysate, or squalene isolated and purified therefrom; and administering the feed additive having the composition to the livestock.

16. A method of making feed additive for livestock, comprising:

preparing a composition comprising, as an active ingredient, the strain of claim 12, a culture product thereof, a cell lysate, or squalene isolated and purified therefrom; and administering the feed additive having the composition to the livestock.

\* \* \* \* \*